（12） United States Patent
Busch et al.

(10) Patent No.: US 7,649,101 B2
(45) Date of Patent: Jan. 19, 2010

(54) PROCESS FOR SELECTIVE OXIDATION OF OLEFINS TO EPOXIDES

(75) Inventors: Daryle H. Busch, Lawrence, KS (US); Bala Subramaniam, Lawrence, KS (US); Hyun-Jin Lee, Lawrence, KS (US); Tie-Pan Shi, Ponca City, OK (US)

(73) Assignee: University of Kansas, Lawrence, KS (US)

( * ) Notice: Subject to any disclaimer, the term of this patent is extended or adjusted under 35 U.S.C. 154(b) by 193 days.

(21) Appl. No.: 11/586,061

(22) Filed: Oct. 25, 2006

(65) Prior Publication Data

US 2007/0093666 A1 Apr. 26, 2007

Related U.S. Application Data (60) Provisional application No. 60/729,941, filed on Oct. 25, 2005.

(51) Int. Cl.
*C07D 301/12* (2006.01)
(52) U.S. Cl. ..................................... 549/531
(58) Field of Classification Search ................ 549/531
See application file for complete search history.

(56) References Cited

U.S. PATENT DOCUMENTS

| | | | |
|---|---|---|---|
| 5,155,247 A | 10/1992 | Herrmann et al. | |
| 5,166,372 A | 11/1992 | Crocco et al. | |
| 5,618,958 A | 4/1997 | Tucker et al. | |
| 5,723,636 A | 3/1998 | Fenelli et al. | |
| 5,939,568 A | 8/1999 | Sharpless et al. | |
| 6,271,400 B2 | 8/2001 | Sharpless et al. | |

FOREIGN PATENT DOCUMENTS

| | | |
|---|---|---|
| EP | 1 346 986 | 9/2003 |
| FR | 2 862 302 | 5/2005 |
| WO | WO 01/77052 A1 | 10/2001 |
| WO | WO 02/085875 A1 | 10/2002 |

OTHER PUBLICATIONS

Rajagopalan et al.; "Homogeneous Catalytic Epoxidation of Organic Substrates in CO 2-Expanded Solvents in the Presence of Water-Soluble Oxidants and Catalysts", Ind. Eng. Chem. Res., vol. 42, No. 25, Dec. 10, 2003, pp. 6505-6510.
European Search Report dated Sep. 23, 2009 for European Patent Application No. 06826630.3; 7pages.

*Primary Examiner*—Taylor Victor Oh
(74) *Attorney, Agent, or Firm*—Stinson Morrison Hecker LLP (57) ABSTRACT

A process for the selective oxidation of olefins to epoxides comprising the step of contacting the olefin (propylene) with an oxidant (hydrogen peroxide) in the presence of a Lewis acid oxidation catalyst (MTO), organic base (pyridine or its N-oxide), in a solvent system comprising an organic water-miscible solvent (methanol); and adding a pressurizing gas (nitrogen) to increase the pressure, whereby olefin is further dissolved in organic solvent system to increase the selectivity and yield of the desired epoxide (propylene oxide).

24 Claims, 6 Drawing Sheets

PROCESS FOR SELECTIVE OXIDATION OF OLEFINS TO EPOXIDES

CROSS-REFERENCE TO RELATED APPLICATIONS

This application is based on and claims priority to U.S. Provisional Application Ser. No. 60/729,941, filed on Oct. 25, 2005, which is hereby incorporated herein by reference.

STATEMENT REGARDING FEDERALLY SPONSORED RESEARCH OR DEVELOPMENT

Not applicable.

BACKGROUND OF THE INVENTION

The epoxidation of olefins, such as propylene to propylene oxide ("PO"), on the industrial scale is among the most challenging chemical processes. Propylene oxide is mainly used for the production of propylene glycol and polyester, and is the starting material for polyurethane, unsaturated resins, and other products.

Industrially over 4.5 million tons of propylene oxide is produced each year using either the chlorohydrin or Halcon process. In the chlorohydrin process, propylene reacts with chlorine and water to produce 1-chloro-2-propanol and HCl, which is then treated with base to generate propylene oxide and salt. There are two pounds of salt waste for each pound of propylene oxide produced. The process consumes large amounts of chlorine and lime which are finally converted to useless and environmentally polluting waste.

The Halcon or hydroperoxide process, organic peroxides are produced, and epoxidation is performed in the presence of transition metal catalysts leading to the formation of propylene oxide and co-products. The economic viability of this process depends on the market value of the co-products because 3 to 4 times more co-product is produced than the weight of propylene oxide produced. Direct oxidation of propylene to propylene oxide with oxygen would be highly desirable, but the presence of propylene's highly reactive allylic hydrogens renders this approach quite difficult.

Minimizing waste in the selective oxidation of propylene to propylene oxide has long been an important objective of industrial chemistry. So-called titanium-substituted silicalite ("TS-1") catalysts can catalyze this reaction with reasonable efficiency using aqueous hydrogen peroxide ($H_2O_2$) and gaseous $O_2/H_2$. TS-1 catalysts have high catalytic activity and selectivity. However, the method is problematic because the catalyst is rapidly deactivated and high temperature is required to regenerate the catalyst. U.S. Pat. No. 5,155,247 entitled "Use of Organorhenium compounds for the oxidation of multiple C—C bonds, oxidation processes based thereon and novel organorhenium compounds" to Herrmann et al. employed a methyltrioxorhenium ($CH_3ReO_3$, hereafter identified as "MTO") catalyst to alkene oxidation under low temperature (below 10° C.) conditions, using hydrogen peroxide as the oxidant. This low temperature process produced propylene oxide and propylene glycol ("PG") in the ratio of 1:1. Herrmann focused on anhydrous hydrogen peroxide (preferably in tert-butanol as a solvent) because water was detrimental to hydrolytic epoxide ring opening. In U.S. Pat. No. 5,166,372 entitled "Epoxidation Process," Crocco et al. improved the selectivity for propylene oxide by employing an alkyl aryl secondary alcohol in the reaction mixture. Magnesium sulfate was used to remove water from the system. In Sharpless, U.S. Pat. No. 5,939,568, nitrogenous aromatic heterocycles were employed as "accelerants" in methylene chloride solvent systems. Lastly, in Sharpless, U.S. Pat. No. 6,271,400, anhydrous oxidants (trialkyl silyl peroxides) and water removal agents were used to reduce the water concentration in the reaction mixture.

The present invention is directed to an olefin oxide synthesis process, such as for the production of propylene oxide, which has a number of advantages over the prior art.

BRIEF SUMMARY OF THE INVENTION

The present invention is directed to a process for the epoxidation of an olefin to the corresponding epoxide using an oxidant, base, catalyst, organic water-miscible solvent, and pressurizing gas. The pressurizing gas is used to drive the olefin substrate into the liquid phase, thereby promoting the yield and rate of the reaction. The present invention preferably occurs at temperatures not exceeding 60° C., and at pressures which increase the concentration of dissolved olefin in the liquid phase.

In a further aspect, the present invention is directed to a reaction mixture. The reaction mixture comprises an olefin to be epoxidized, an oxidant, a Lewis acid oxidation catalyst, and an organic base in a solvent system comprising an organic water-miscible solvent. A pressurizing gas (e.g. between about 230 to 700 psi) is added so that the olefin is partially dissolved in the organic solvent system in a higher amount than without the pressurizing gas.

In one aspect, the olefin is ethylene or propylene, the catalyst is an organorhenium oxide, and the oxidant is hydrogen peroxide in an aqueous solution having about 20 to 80 wt % hydrogen peroxide or is urea hydrogen peroxide. The pressurizing gas preferably an inert gas, such as nitrogen having a pressure between about 230 and 700 psi. The organic base is also preferable a nitrogen-containing compound selected such as pyridine and/or its corresponding N-oxide. The water miscible solvent is preferably a lower alcohol, such as methanol. In the case of aqueous hydrogen peroxide oxidants, the water associated with the hydrogen peroxide system will form part of the overall solvent system (along with water produced as a result of the decomposition of the hydrogen peroxide). Preferably the solvent system comprises methanol and water at a weight ratio between 3:1 to 22:1 for methanol to water. The reaction preferably occurs at a temperature of about 20 to 30° C.

In another aspect, methods for separating the epoxidized product and recycling the unreacted reactants is provided. For example, in one aspect, the pressure of the system may be decreased to create a vapor phase containing unreacted olefin and a liquid phase comprising the epoxidized olefin, Lewis acid oxidation catalyst, and solvent system. The liquid phase may be fractionated to distill off a first gaseous stream comprising the epoxidized olefin and a second liquid stream comprising the Lewis oxidation catalyst, organic base, and solvent system.

In still another aspect, the water may be separated from the Lewis oxidation catalyst, said organic base, and organic water miscible solvent from the second liquid stream by reverse osmosis. The oxidation catalyst, organic base, and/or organic water miscible solvent may be recycled to the feed stream.

In yet another aspect, the oxidation catalyst, organic base, and and/or organic water miscible solvent are separated from the second liquid stream by distillation. Again, the oxidation catalyst, organic base, and/or organic water miscible solvent may be recycled to the feed stream.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

The present invention is directed to a process for epoxidizing an olefin comprising the steps of (1) contacting the olefin with an oxidant in the presence of a Lewis acid oxidation catalyst, organic base, in a solvent system comprised an organic water-miscible solvent; and (2) adding a pressurizing gas to increase the pressure, whereby the olefin is further dissolved in said organic solvent system.

The olefins epoxidized in the process of the present invention may be any organic compound having at least one ethylenically unsaturated functional group (i.e., a carbon-carbon double bond) and may be, for example, an aromatic, aliphatic, mixed aromatic-aliphatic (e.g., aralkyl), cyclic, branched or straight chain olefin. Examples are set forth in Sharpless et al., U.S. Pat. Nos. 5,939,568 and 6,271,400, which are incorporated by reference. Preferably, the olefin contains from 2 to 30 carbon atoms (i.e., a $C_2$-$C_{30}$ olefin). More than one carbon-carbon double bond may be present in the olefin, and thus, dienes, trienes, and other polyunsaturated substrates thus may be used. Other examples of suitable substrates include unsaturated fatty acids or fatty acid derivatives such as esters or glycerides and oligomeric or polymeric unsaturated compounds such as polybutadiene. The olefin may optionally contain substituents other than hydrocarbon substituents such as halide, carboxylic acid, ether, hydroxy, thiol, nitro, cyano, ketone, ester, anhydride, amino, and the like.

Exemplary olefins suitable in the process of the present invention include ethylene, propylene, the butenes, butadiene, the pentenes, isoprene, 1-hexene, 3-hexene, 1-heptene, 1-octene, diisobutylene, 1-nonene, 1-tetradecene, pentamyrcene, camphene, 1-undecene, 1-dodecene, 1-tridecene, 1-tetradecene, 1-pentadecene, 1-hexadecene, 1-heptadecene decene, 1-nonadecene, 1-eicosene, the trimers and tetramers of propylene, polybutadiene, polyisoprene, cyclopentene, cyclohexene, cycloheptene, cyclooctene, cyclooctadiene, cyclododecene, cyclododecatriene, dicyclopentadiene, methylenecyclopropane, methylenecyclopentane, methylenecyclohexane, vinylcyclohexane, vinyl cyclohexene, methallyl ketone, allyl chloride, allyl bromide, acrylic acid, methacrylic acid, crotonic acid, vinyl acetic acid, crotyl chloride, methallyl chloride, the dichlorobutenes, allyl alcohol, allyl carbonate, allyl acetate, alkyl acrylates and methacrylates, diallyl maleate, diallyl phthalate, unsaturated triglycerides such as soybean oil, and unsaturated fatty acids, such as oleic acid, linolenic acid, linoleic acid, erucic acid, palmitoleic acid, and ricinoleic acid and their esters (including mono-, di-, and triglyceride esters), and alkenyl aromatic compounds such as styrene, .alpha.-methyl styrene, .beta.-methyl styrene, divinyl benzene, 1,2-dihydronaphthalene, indene, stilbene, cinnamyl alcohol, 2-methyl-1-phenyl-1-propene, 2-methyl-3-phenyl-2-propen-1-ol, cinnamyl acetate, cinnamyl bromide, cinnamyl chloride, 4-stilbenemethanol, ar-methyl styrene, ar-ethyl styrene, ar-tert-butyl styrene, archlorostyrene, 1,1-diphenylethylene, vinyl benzyl chloride, vinyl naphthalene, vinyl benzoic acid, ar-acetoxy styrene, ar-hydroxy styrene (i.e., vinyl phenol), 2- or 3-methyl indene, 2,4,6-trimethylstyrene, 1-phenyl-1-cyclohexene, 1,3-diisopropenyl benzene, vinyl anthracene, vinyl anisole, and the like. Of these, propylene and ethylene are most preferred. The olefin is preferably present in about 2 to 20 mol % of the reaction mixture. It will be appreciated to those skilled in the art that the olefin concentration (i.e., availability) in the liquid phase, where the reaction occurs, is most important, and for low boiling light olefins this is dictated by the operating pressure and temperature. The liquid phase preferably contains at least a stoichiometric amount of the oxidant required to make complete olefin (e.g. propylene) conversion to epoxide (e.g. propylene oxide) possible.

The oxidant used in the present invention comprises hydrogen peroxide. Hydrogen peroxide is typically commercially available in the form of a solid urea (anhydrous) form or aqueous solution, typically 30 to 50 wt % is commercially available. Thus, as discussed more fully below, that water may form part of the overall solvent system of the reaction mixture, along with a suitable organic water-miscible solvent. The oxidant is preferably present in the reaction mixture at a concentration of about 4 to 16 mol %. As discussed above, the oxidant is present in a stoichiometric amount for complete epoxidation of the olefin (e.g. propylene to propylene oxide) to occur.

The base used in the present invention preferably comprises a saturated or unsaturated amine or corresponding N-oxide. Examples are set forth in Sharpless, U.S. Pat. Nos. 5,939,568 and 6,271,400, which are incorporated by reference. Suitable organic nitrogen bases are, for example, methylamine, diethylamine, propylamine, octylamine, trimethylamine, dimethyldodecyl amine, cyclohexyl amine, dicyclohexylamine, aminoethanol, diethanolamine, triethanolamine, N,N-dributylethanolamine, ethylenediamine, hexamethylenediamine, morpholine, piperidine, pyridine, substituted pyridines, 2,2'-bipyridine and 2,2',2"-tripyridine and their substituted derivatives, imidazole and triazines, and corresponding N-oxides. Of these, pyridine and pyridine N-oxide are most preferred. The amount of base may be determined by the catalyst concentration, and the molar amount of based should be at least the molar equivalent of the catalyst. Typically, the amount of base is about 0.1 to 0.56 mol % with 0.2% being preferred.

The catalyst used in the present invention is preferably a Lewis acid oxidation catalyst, such as organorhenium oxide catalysts (e.g., methyltrioxorhenium), or other high valent rhenium-containing compound. Other suitable but less preferred catalysts include those based on tungsten (e.g., tungstates), molybdenum (e.g., molybdates), and titanium(IV) compounds and vanadium(IV) or vanadium(V) compounds. Such compounds are known to those skilled in the art, and examples are set forth in U.S. Pat. Nos. 5,166,372; 5,155,247; 5,939,568 and 6,271,400, which are incorporated by reference. Typically, about 0.05 to 0.08 mole % of MTO and other catalysts is used. The preferred molar olefin to catalyst ratio is between about 40:1 and 400:1.

The organic water-miscible solvent used in the epoxidation process of the present invention is preferably a lower alcohol ($C_1$-$C_4$), e.g., methanol, ethanol, propanol, isopropanol, tert-butanol, and the like. Other exemplary solvents are those set forth in U.S. Pat. Nos. 5,939,568 and 6,271,400, with tetrahydrofuran, acetonitrile, and aromatic hydrocarbons such as toluene and xylene being preferred. Of these, methanol is especially preferred. In one aspect, the methanol:water weight ratio ranges from 3:1 to 22:1 methanol over water, with weight ratios of 13:1 to 22:1 being preferred. It will be appreciated that water may be present in the initial reaction mixture (e.g. from aqueous hydrogen peroxide) and may also be produced by decomposition of the hydrogen peroxide during the reaction itself.

The pressurizing gas used in the present invention is preferably an inert gas (such as nitrogen, argon, neon, helium, and the like). The pressure ranges between about 100 and 1000 psi, although pressures between about 230 and 700 psi are most preferred.

Figure 1:
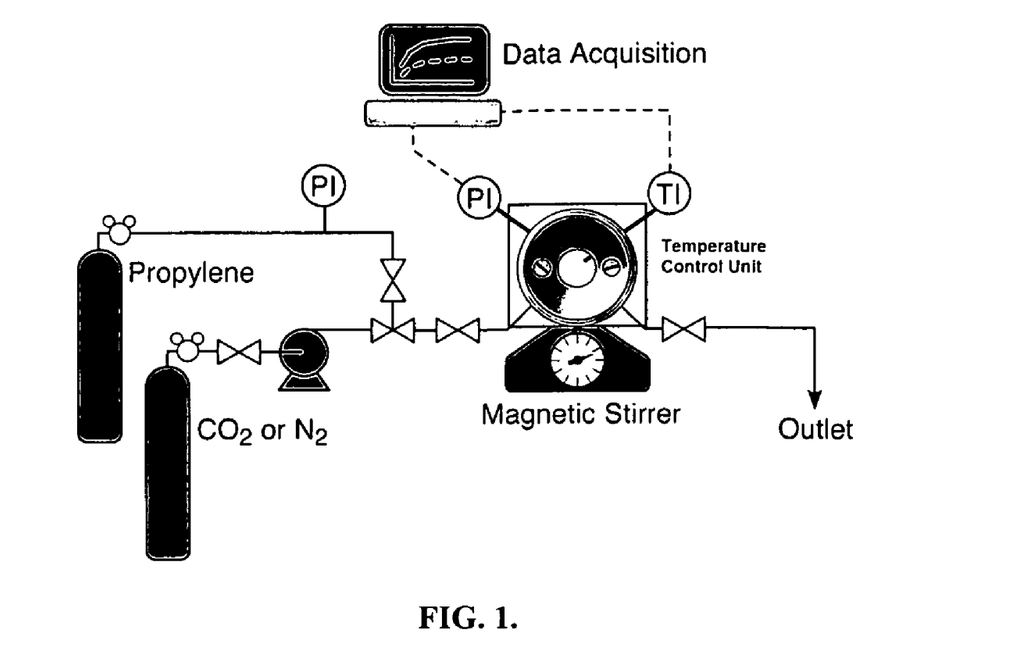
FIG. 1 is a schematic of the reactor used in all examples except Example 2 of the present invention.

For the following examples, a cylindrical view-cell reactor as generally set forth in FIG. 1 was constructed. The reactor was made of titanium and has two end caps fitted with two sapphire windows, a gas inlet valve, and a gas outlet valve as shown in FIG. 1. The reactor was interfaced with a pressure transducer, a thermocouple, and a pressure relief valve. The pressure and temperature were computer-monitored during the reaction. The reactor was heated with a band heater for the 1, 3, 6, and 12-hour reaction periods in fixed-time batch experiments.

As discussed in the following examples, introduction of the pressurizing inert gas intensified the reaction, producing high yields of the desired epoxide product. The inert gas preferentially partitions the olefin (e.g., propylene) into the liquid phase. The yield is greater than 50% propylene oxide, even more preferably greater than 75%, still even more preferably greater than 90%, and most preferably greater than 95% and even greater than 99%.

EXAMPLE 1

Oxidation of Propylene with Carbon Dioxide as the Pressurizing Gas

In this example, the effect of adding dense carbon dioxide to the reaction mixture was investigated in various organic solvent systems and bases. More specifically, in this example, the reactor was charged with 0.0120 g (0.049 mmol) MTO, 0.610 ml aqueous hydrogen peroxide (50 wt % in water, density 1.18 g/ml) (10.58 mmol) in either 4.14 ml methanol or 4.0 ml acetonitrile as the organic solvent, with 0.40 ml (4.965 mmol) pyridine or 0.049 g (0.51 mmol) pyridine N-oxide as the base.

After introduction of 100 mg (2.376 mmol) propylene, carbon dioxide (2.37 ml, about 700 psi at 25° C.) was then added to the reactor by bubbling through the liquid at a predetermined pressure (700 psi) selected to produce a single liquid phase in the reactor. In addition to the carbon dioxide pressure, the reaction mixture compositions were chosen to produce a single liquid phase in the reactor. The reaction was monitored for about three hours at about 40° C.

At the conclusion of the reaction period, the propylene oxide was separated by a simple distillation method and the amount of the propylene oxide was determined by gas chromatography ("GC") or GC combined with mass spectrometry ("GC/MS").

As shown in Table 1 below, the highest yield of propylene oxide was produced with a methanol/water as the solvent system and pyridine N-oxide as the base. It should be noted that the water that forms part of the solvent system comprises both the water in the aqueous hydrogen peroxide reactant solution and water formed as part of the hydrogen peroxide decomposition during the reaction. The high solubility of propylene in methanol produces the higher yield of propylene oxide than that obtained with acetonitrile. The selectivity favors propylene oxide as the product by over 95% in all cases using methanol as the organic solvent. Trace amounts of propylene glycol in the $CO_2$/acetonitrile example or 1-methoxy-2-propanol in the $CO_2$/methanol example were produced during the reactions (data not shown).

TABLE 1

Propylene oxidation with $CO_2$ Expanded Liquid Solvent System

| Ex. | Base | Organic solvent | Yield of PO (%) | Selectivity (%) |
|---|---|---|---|---|
| 1 | None | Acetonitrile | 14.65 | N/A |
| 2 | Pyridine | Acetonitrile | 18.20 | N/A |
| 3 | Pyridine | Methanol | 60.25 | 98 |
| 4 | Pyridine N-oxide | Methanol | 78.73 | 96 |

EXAMPLE 2

Propylene Solubility in Methanol/Water Solvent System at Different Pressures

Figure 2:
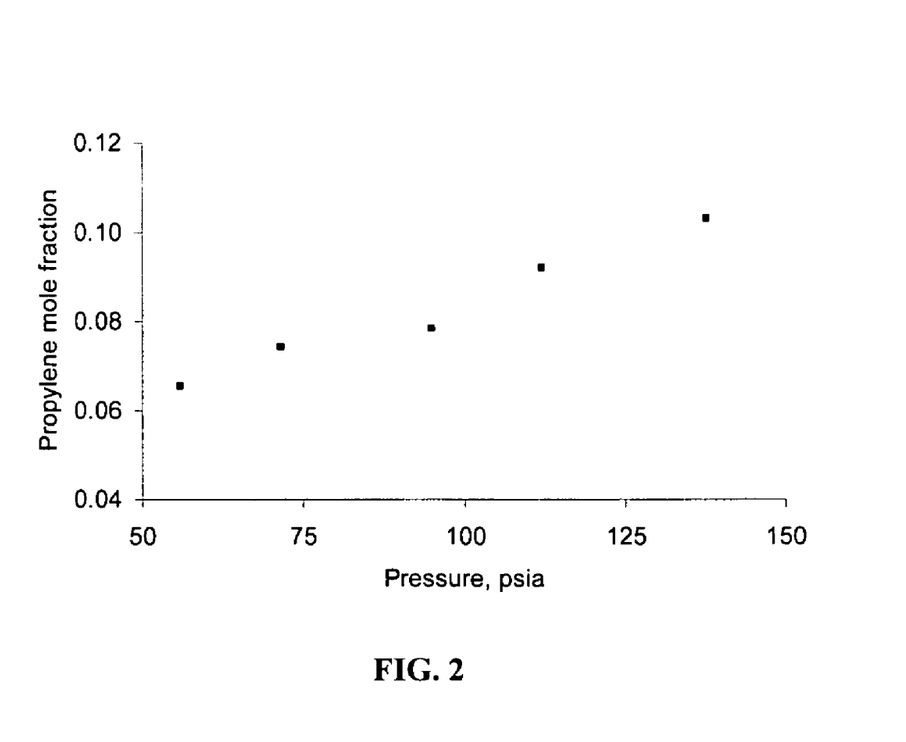
FIG. 2 shows propylene solubility in a methanol/water (6:1 wt ratio) medium as a function of propylene pressure.

In this example, the propylene solubility in the methanol/water solvent system was investigated at different pressures. A methanol/water weight ratio of 6:1 was used in this example. In this example, propylene was fed to the reactor to reach various system pressures by adjusting the amount of propylene. The solubility of propylene in the liquid phase was measured by GC equipped with both capillary and packed columns. At 40° C., the mole fraction of propylene in the liquid phase is shown in FIG. 2 and increases, as expected, with applied propylene pressure.

EXAMPLE 3

Effects of Different Bases on Propylene Oxide Yield and Selectivity

In this example, several different organic nitrogen-containing bases were investigated to determine effects on yield and selectivity. More specifically, in this example, the reactor was charged with 0.0120 g (0.049 mmol) MTO, 0.610 ml aqueous hydrogen peroxide (50 wt % in $H_2O$) in 4.14 ml methanol as the organic solvent and a base as set forth in Table 2 below. Carbon dioxide (700 psi) was added as in Example 1. The bases tested included pyridine, pyridine N-oxide, 4,4'-dipyridyl, 2,2'-dipyridyl N,N'-dioxide, 2,2'-6,2"-terpyridine, 2,4,6-tri(4-pyridyl)-1,3,5-triazine, and diphenylamine were studied in search of the optimal co-factor for propylene oxidation. As shown in the table below, pyridine-N-oxide produced the highest yield in methanol at 40° C. in the presence of 700 psi carbon dioxide.

TABLE 2

Base Effect of Propylene Oxidation with MTO for 3-Hour Reaction in Carbon-Dioxide Expanded Liquid

| Ex. | Base | Amount | Yield of PO (%) | Temp (° C.) | Reaction time (hour) |
|---|---|---|---|---|---|
| 3 | Pyridine | 0.40 ml (4.96 mmol) | 60.25 | 40 | 3 |
| 4 | Pyridine N-oxide | 48.8 mg (0.512 mmol) | 72.73 | 40 | 3 |
| 5 | Pyridine N-oxide | 9.76 mg (0.102 mmol) | 51.10 | 40 | 9 |
| 6 | Diphenylamine | 23.1 mg (0.137 mmol) | 31.48 | 40 | 3 |
| 7 | 2,2'-Dipyridyl N,N'-dioxide | 10.8 mg (0.057 mmol) | 50.34 | 30 | 3 |
| 8 | No base | | 51.08 | 40 | 3 |

EXAMPLE 4

Effect of Nitrogen as Pressurizing Gas on Yield and Selectivity

In this example, the effect of using nitrogen as the pressurizing gas was investigated. More specifically, in this example, the reactor was charged with 0.0120 g (0.049 mmol) MTO, 0.27 ml aqueous hydrogen peroxide (50 wt % in $H_2O$) (4.685 mmol) in 4.14 ml methanol as the organic solvent, and 0.049 g (0.512 mmol) pyridine N-oxide as the base.

After the propylene (100 mg) was charged into the reactor, pressurized nitrogen was added to give a pressure equivalent to that in previous reactions using a carbon dioxide pressurized system (700 psi). Various nitrogen pressures were examined as shown in the table below. For each experiment, the reaction time was about 3 hours (error ±5%), and the temperature was maintained at about 40° C.

TABLE 3

Nitrogen and pressure effect for propylene oxidation.

| Ex. | Pressurizing Gas | Pressure | Yield of PO (%) | Selectivity | By-Products (wt %) |
|---|---|---|---|---|---|
| 4 | $CO_2$ | ~700 psi | 72.73 | >95 | 1.85% 1M2P 0.59 PG |
| 9 | $N_2$ | ~700 psi | >99 | >95 | 2.3% 1M2P |
| 10 | $N_2$ | ~230 psi | >98 | >95 | 1.02% 1M2P |
| 11 | None | ~35 psi | 82.58 | >95 | |

* PG = propylene glycol; 1M2P = 1-methyl-2-propanol

EXAMPLE 5

Effect of Nitrogen As Pressurizing Gas on Substrate Solubility

The reactor pressure with propylene (100 mg) and water was about 90 psi (data not shown). As shown in the Table 3 above, when methanol (instead of water alone) was used as a co-solvent, the reactor pressure with methanol is reduced by about 55 psi to only 35 psi because of the solubility of propylene in the methanol/water solvent system.

Figure 3:
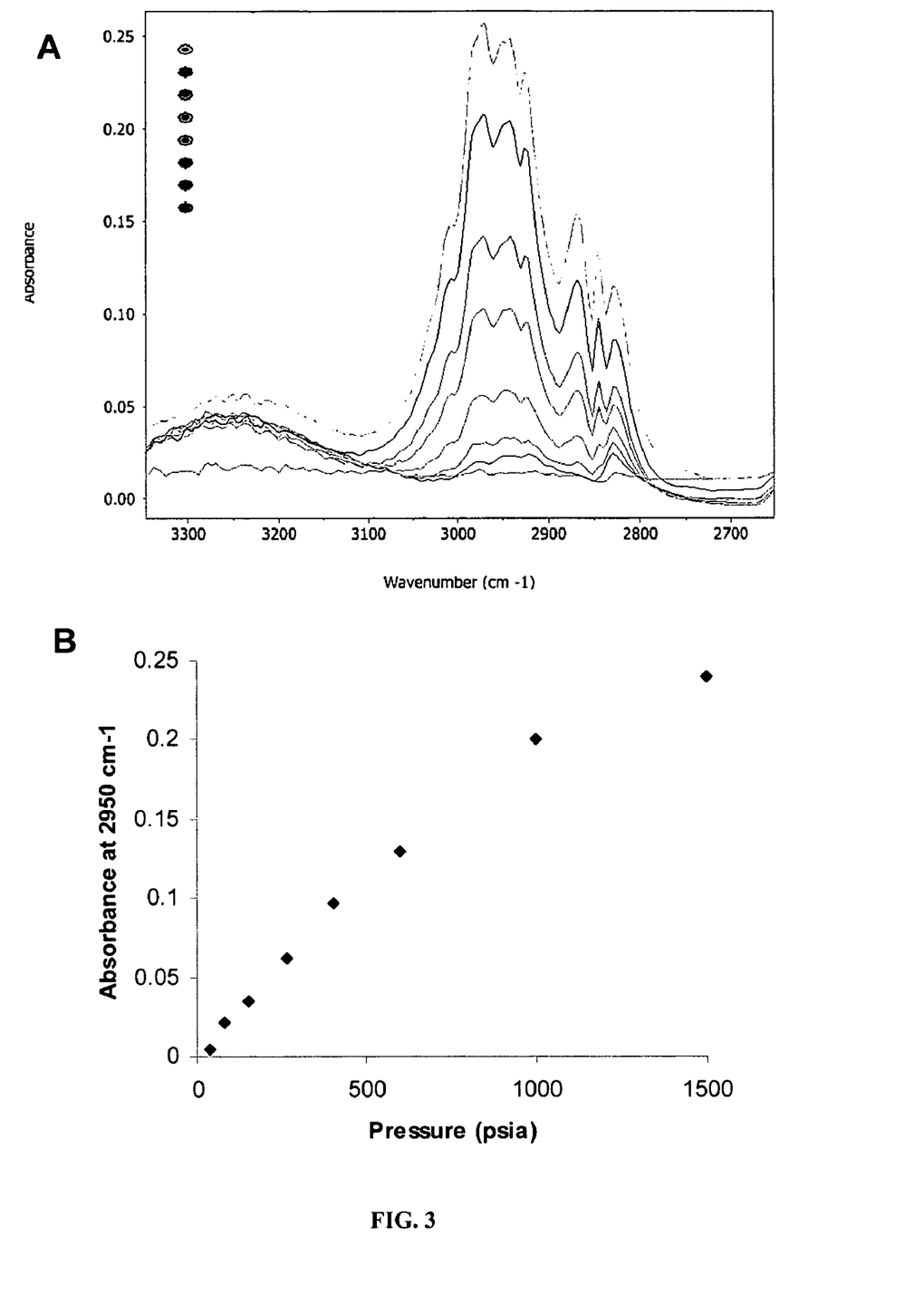
FIG. 3 shows the alkene C—H stretching vibration band around 3000 cm$^{-1}$ at various pressures. Spectral changes due to pressure increases indicate the increased solubility of propylene.

The foregoing examples suggest that increased conversion at higher nitrogen pressures should be attributed in part to enhanced, propylene solubility in methanol. Indeed, as shown in FIG. 3, in situ ReactIR studies in a stirred vessel show that the concentration of propylene in the liquid methanol/water phase at progressively increasing nitrogen pressures.

To test this, experimental measurements reveal increased propylene solubility, albeit modest, in the liquid phase under increasing nitrogen pressure. The experiments were performed with a 6:1 weight methanol/water liquid phase mixture. The temperature was held at 40° C. and the propylene partial pressure in the gas phase was maintained constant at nearly 44 psi. The total pressure of the system was then increased by adding various partial pressures of nitrogen and then measuring the equilibrium propylene solubility in the liquid phase. The results are as shown in Table 4:

TABLE 4

Propylene solubility in Methanol/Water (6:1 weight ratio) medium at 40° C.

| Pressure (psi) | Propylene solubility in liquid phase (mole fraction) |
|---|---|
| 44 psi propylene | 0.0623 |
| 44 psi propylene + 105 psi $N_2$ | 0.0680 |
| 44 psi propylene + 206 psi $N_2$ | 0.0715 |

The enhanced solubility of propylene under pressurized nitrogen increases the yield of propylene oxide over that found for the reaction in the carbon dioxide pressurized system or with no added gas.

EXAMPLE 6

Effect of Solvent on Product Yield

Figure 4:
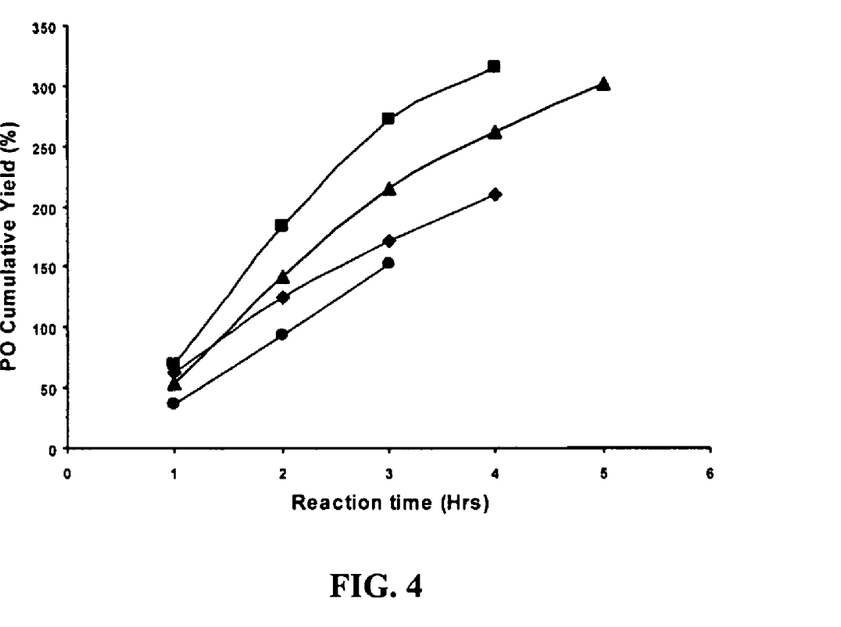
FIG. 4 shows the effect of solvent on propylene oxidation (■: $CH_3OH$; ▲: tert-BuOH; ♦: $CH_3CN$; ●: isopropanol).

In this example, the effect of various organic solvents on product yield was investigated. Several different alcohols, including methanol, isopropanol and tert-butanol, and acetonitrile ($CH_3CN$), were used to test catalyst stability. The reactor was charged with MTO (0.0120 g, 0.049 mmol), pyridine-N-oxide (0.0144 g, 0.151 mmol) and 0.27 ml aqueous hydrogen peroxide (50 wt % in $H_2O$) (4.684 mmol) in 4.14 ml of one of the organic solvents. Propylene (100 mg, 2.376 mmol) was charged into the reactor which was then pressurized with $N_2$ at 30° C. at 250 psi. In order to repeat the reaction, fresh propylene and $H_2O_2$ were added to the reactor after the first 1-hour reaction. Products were analyzed by GC at the end of each 1-hour cycle. The order of catalyst stability was then judged by the cumulative product yield: isopropanol<acetonitrile<tert-butanol<methanol, as shown in FIG. 4.

EXAMPLE 7

Effect of Temperature on Product Yield

In this example, the effect of reaction temperature on product yield was investigated. More specifically, propylene oxidation with MTO was carried out at 20, 30, and 40° C. The reactor was charged with MTO (0.0120 g, 0.049 mmol), pyridine N-oxide (0.0144 g, 0.151 mmol) and 0.27 ml aqueous hydrogen peroxide (50 wt % in $H_2O$) (4.684 mmol) in 4.14 ml of methanol as the organic solvent. The propylene (100 mg, 2.376 mmol) was charged into the reactor which was then pressurized with $N_2$ at 250 psi. Fresh propylene and $H_2O_2$ was added after each 1-hour reaction and products were monitored by GC.

Figure 5:
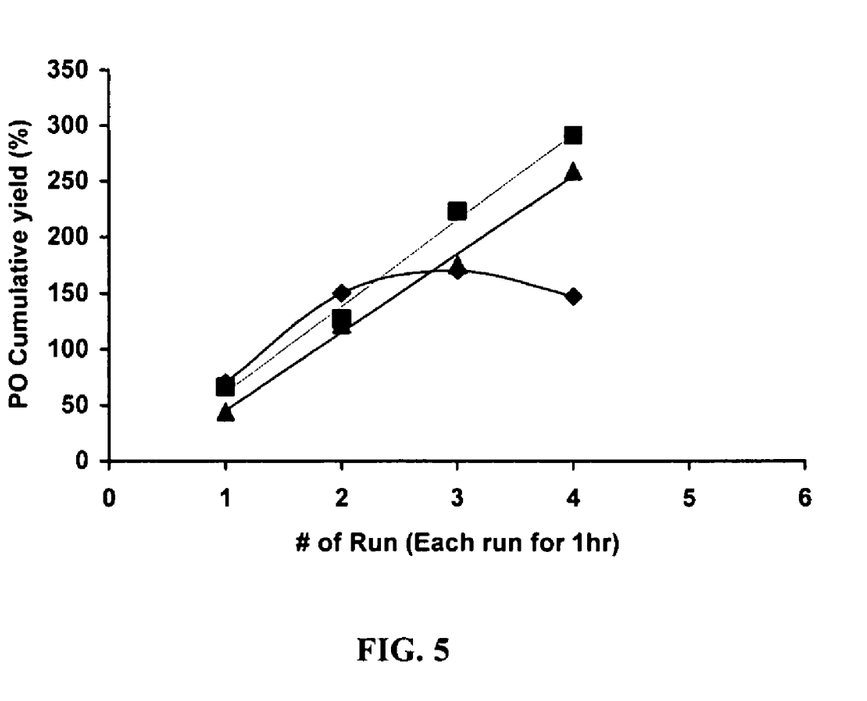
FIG. 5 shows the effect of temperature on propylene oxidation (■: 30° C.-pyNO: color disappeared after 12 hrs; ▲: 20° C.-pyNO; ♦: 40° C.-pyNO: color disappeared after third run).

The results are shown in FIG. 5. On the time scale of these reactions, the optimal reaction temperature is between about 20 and 30° C. In the course of these studies, it became apparent that the color of the solution is a strong indicator of the condition of the catalyst. In accord with the literature (M. Abu-Omar, P. J. Hansen, J. H. Espenson, *J. Am. Chem. Soc.*, 1996, 4966-4974), the solution maintains a yellow color so long as the diperoxo derivative of MTO is the dominant species in solution. As long as this color is stable, the catalyst performance is stable. Significantly, the color of the solution studied at 20° C. remained a strong yellow even though the cumulative yield of product was uniformly a little lower than that for the system operating at 30° C. It is important to note that the latter solution became colorless after approximately 12 hours. These results indicate that the catalyst, while exhibiting higher propylene oxide formation activity at higher temperatures, also deactivates more rapidly at those temperatures. Decreasing the temperature had a clear beneficial effect on the stability of the MTO catalyst as revealed by the cumulative yield of propylene oxide.

EXAMPLE 8

Effect of Peroxide Source on Product Yield

By the very nature of the hydrogen peroxide source, the 50% aqueous solution, all of the studies described above were conducted in a partial aqueous media. In order to provide an evaluation of the effect of the water component of the solvent system on the process, solid urea hydrogen peroxide was used as the hydrogen peroxide source during the reaction. The reactor was charged with MTO (0.0120 g, 0.049 mmol), pyridine N-oxide (0.0144 g, 0.151 mmol) and solid urea hydrogen peroxide (4.684 mmol) or 0.27 ml aqueous hydrogen peroxide (50 wt % water) (4.684 mmol) in 4.14 ml of methanol or tert-butanol. The propylene (100 mg, 2.376 mmol) was charged into the reactor which was then pressurized with $N_2$ (about 250 psi) and heated at 30° C.

Figure 6:
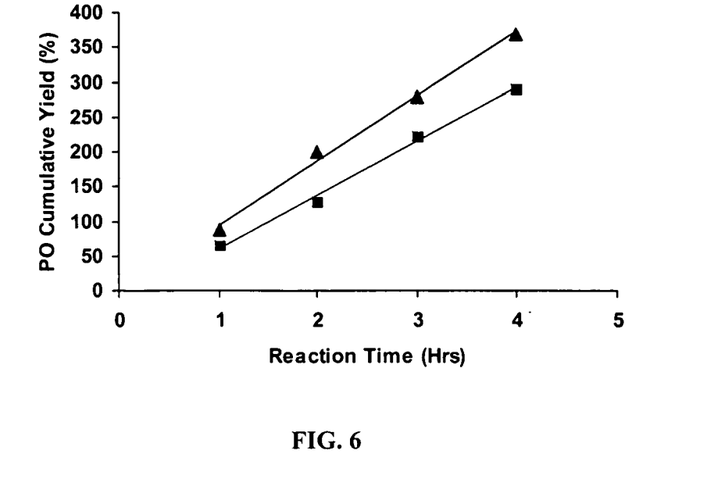
FIG. 6 shows aqueous vs. dry reaction conditions (■: with $H_2O_2$ in 50 wt % $H_2O$; ▲: with urea hydrogen peroxide).

In most of the experiments described herein, the system contained a significant amount of water due to use of 50 wt % hydrogen peroxide in water. The methanol/water ratio did not significantly affect the yield (data not shown), but the yield of PO was substantially increased in the reactions using the dry source of hydrogen peroxide (urea hydrogen peroxide) in methanol, as shown in FIG. 6.

Figure 7:
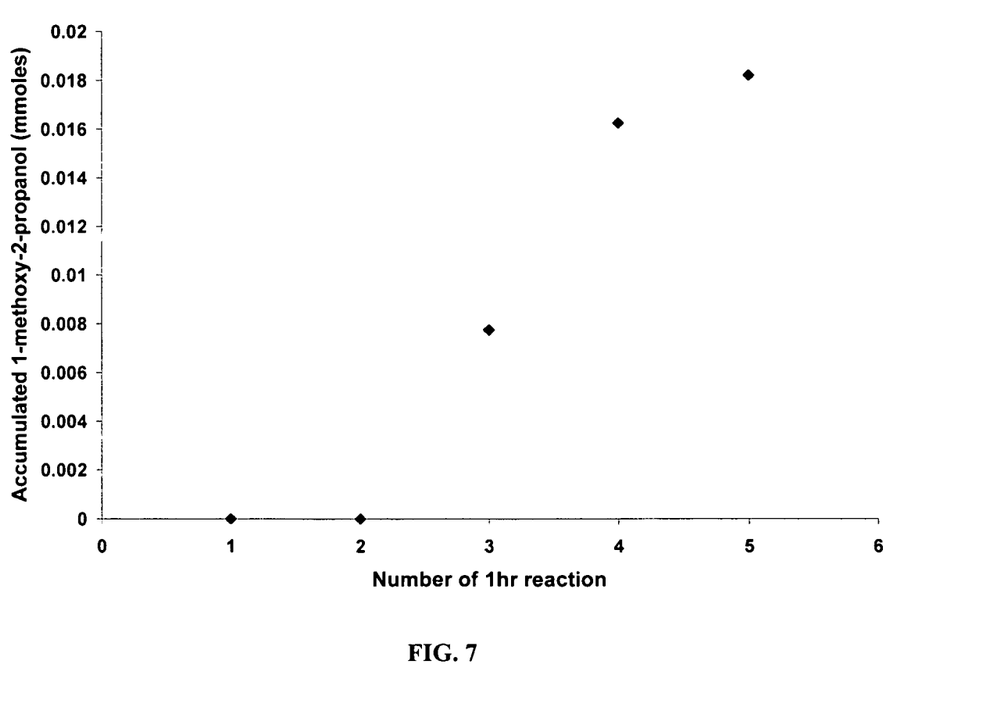
FIG. 7 shows the amount of 1-methoxy-2-propanol byproduct with decreasing methanol/water ratios in continuous reaction data at 1-hour reaction period increments with new propylene and oxidant feed.

The amount of 1-methoxy-2-propanol byproduct was affected by the methanol/water ratio. FIG. 7 shows continuous reaction data for five continuous one-hour reaction periods. Reactants were placed in the reactor as in previous examples, and the reaction was allowed to proceed for 1-hour periods at 30° C. The products were then analyzed by GC. Fresh propylene and 50 wt % hydrogen peroxide were added to the same reactor, and the reaction was continued for another 1-hour reaction. Water accumulates during each reaction period due to the additional water formation from hydrogen peroxide decomposition. FIG. 7 clearly shows increasing concentrations of the unwanted by product 1-methoxy-2-propanol with increasing amounts of water in the solvent system. Thus, the selectivity of propylene oxide production decreased slightly for longer reaction times.

EXAMPLE 9

Other Olefinic Substrates

In this example, the MTO system was applied to the oxidation of ethylene as the olefin. The reactor was charged with MTO (0.0204 g, 0.082 mmol), pyridine N-oxide (0.02 g, 0.210 mmol) and 0.27 ml aqueous hydrogen peroxide (50 wt % in $H_2O$) (4.684 mmol) in 4.0 ml of methanol as the organic solvent. The ethylene (100 mg, 2.376 mmol) was charged into the reactor which was then pressurized with about 300 psi nitrogen and the reactor was heated at 30° C. After a 3-hour batch reaction, ethylene oxide was found as the product with no sign of byproducts such as ethylene glycol.

EXAMPLE 10

Other Catalyst Systems

Earlier studies found that tungstate catalysts obtained excellent conversion and selectivity for alkene epoxidation. See Sato et al., *A "Green" Route to Adipic Acid. Direct Oxidation of Cyclohexenes with* 30 *Percent Hydrogen Peroxide*, J. Org. Chem. 1996, 61, 8310-8311; Maheswari et al., *A $Na_2WO_4/H_2WO_4$-Based Highly Efficient Biphasic Catalyst towards Alkene Epoxidation, using Dihydrogen Peroxide as Oxidant*, Adv. Synth. Catal. 2005 347, 1759-1764. Strong Lewis acid catalysis is expected since W(VI) is also a high oxidation state. The inorganic tungstate anion is also very stable in the presence of oxidizing agents and at high reaction temperatures. It should also be easily recovered and recycled post reaction. $Na_2WO_4.2H_2O$ and $H_2WO_4$ were applied for propylene oxidation under various conditions as shown Table 6.

TABLE 6

| Chemical compositions for studies on tungstate catalysts | |
|---|---|
| Propylene | 0.1 g (4.76 mmoles) |
| Organic solvents | $CH_3OH$, $CH_3CN$ (4.0 ml) |
| Catalysts | 0.026 g $Na_2WO_4 \cdot 2H_2O$ (0.078 mmol) |
| | 0.022 g $H_2WO_4$ (0.087 mmol) |
| Phase transfer reagent | Aliquat 336 |
| | 0.5 ml |
| Temperature | 30–70° C. |
| $N_2$ Pressure | 300–800 psi |
| Oxygen source | 1 ml of $H_2O_2$ (50 wt. % in $H_2O$) |

Dissolving tungstic acid in organic solvents presented challenges and may be responsible for the slow reactions indicated by the data in Table 6. The catalysts solubility issue was resolved by using $NH_4OH$ to dissolve the acid, followed by the addition of a strong mineral acid to provide the low pH desired for the solutions.

The reactor was charged with 0.0522 g $Na_2WO_4.2H_2O$ (0.158 mmol), $H_2WO_4$ (0.052 mg, 0.207 mmol) or mixture of 0.026 g $Na_2WO_4.2H_2O$ (0.078 mmol)/0.022 g $H_2WO_4$ (0.087 mmol), 0.0602 mg of chloroacetic acid $ClCH_2COOH$ and 1.0 ml of aqueous hydrogen peroxide (50 wt % in $H_2O$) in 4 ml of methanol as shown in Table 6. Propylene (100 mg, 2.376 mmole) was charged into the reactor which was then pressurized with about 300 psi nitrogen and heated at 40-90° C. The peroxide was rapidly decomposed above 60° C. The catalyst dissolved completely in Experiment 1 which displayed a clear yellow color. The catalyst mixture was only partially dissolved in the $CH_3OH/ClCH_2COOH$ medium in Experiments 3-5. The mixture of catalysts was dissolved in $CH_3OH$ with $NH_4OH$ to improve solubility and a limited amount of $H_2SO_4$ was added in the systems 4 and 5 to return to acidic conditions.

TABLE 7

Propylene oxidation conditions with $Na_2WO_4 \cdot 2H_2O/H_2WO$

| Ex | Catalysts | Additive | Temperature | Products | PO yield |
|---|---|---|---|---|---|
| 1 | $Na_2WO_4 \cdot 2H_2O$ | | 40° C./300 psi $N_2$ | PO | 2%/4 hr |
| 2 | $H_2WO_4$ | | 40° C./300 psi $N_2$ | PO + PG | 5.7%/4 hr |
| 3 | $Na_2WO_4 \cdot 2H_2O/H_2WO$ | | 40° C./300 psi $N_2$ | PO + PG | 1.5%/12 hr |
| 4 | $Na_2WO_4 \cdot 2H_2O/H_2WO$ | $NH_4OH/H_2SO_4$ | 40° C./300 psi $N_2$ | PO + PG | 1.0%/12 hr |
| 5 | $Na_2WO_4 \cdot 2H_2O/H_2WO$ | Aliquat 336 | 40° C./300 psi $N_2$ | PO + PG | |

This example thus shows that the epoxidation can occur with very different catalysts, and at very mild conditions. It will be appreciated that those skilled in the art will be able to optimize conditions to further improve the performance of the catalysts discussed herein.

EXAMPLE 11

Catalyst, Base, and Co-Solvent Recycle

Figure 8:
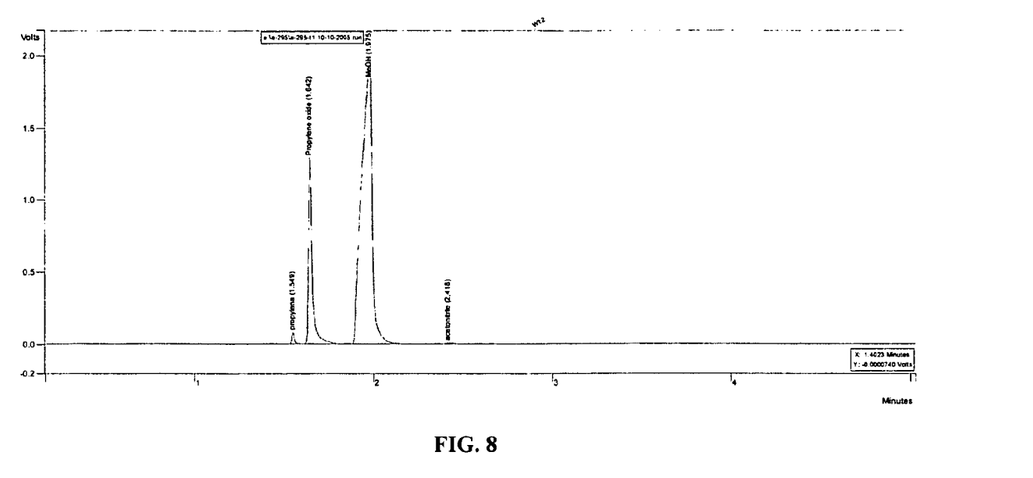
FIG. 8 shows the gas chromatograph results of the separated propylene oxide from Example 11 by simple distillation.

In this example, two methods were applied to evaluate the MTO catalyst recycle. First, a simple distillation was performed at 50° C. after the 3-hour reaction as follows. The reactor was charged with MTO (0.0240 g, 0.098 mmol), pyridine-N-oxide (0.3 g, 0.315 mmol), and 1 ml aqueous hydrogen peroxide (50 wt % in $H_2O$) (17.35 mmol) and then charged with 0.3 ml of propylene (7.13 mmol) in a 4.14 ml methanol solvent system and 250 psi nitrogen. The reactor was depressurized to ambient pressure followed by heating of the reaction mixture. At about 40 to 50° C., the propylene oxide boils off leaving the remaining liquid reaction mixture containing mostly water, methanol and dissolved catalyst. The vapor phase propylene oxide is condensed and collected in a dry ice acetone trap. The GC chromatogram after a single stage distillation step shows the efficient separation of propylene oxide from the reactor (FIG. 8). The separated products contain some methanol but multiple stage distillation will improve separation. Secondly, all liquid chemical reagents and the recovered catalyst were dried. The recovered catalyst was reused in the subsequent reaction.

Figure 9:
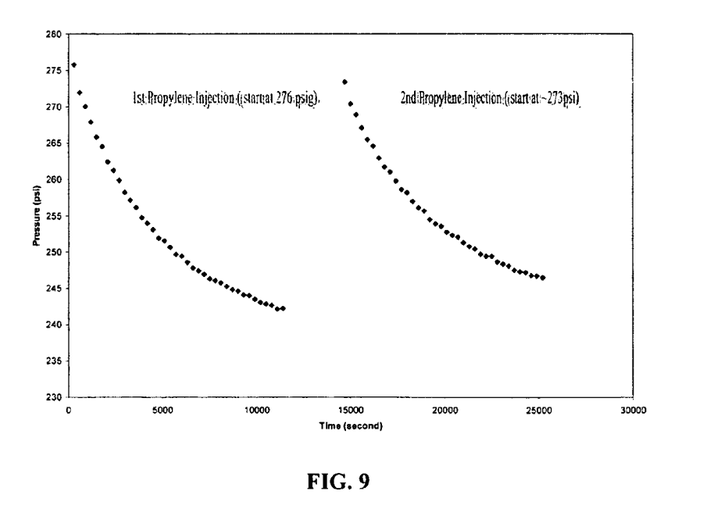
FIG. 9 shows the pressure change between two consecutive reaction cycles. Fresh propylene was charged after the first three-hour reaction.

The stability of the catalyst was examined by multi-cycle reactions. The first reaction was carried out for 3 hours at 40° C. and products were separated by the simple distillation method and the same amount of fresh propylene was charged in a second reaction cycle. The second reaction was carried out under the same conditions as the first reaction but no hydrogen peroxide and methanol was added. The observed decrease in reactor pressure for the two sequential reactions is almost identical, as shown in FIG. 9. The only gaseous substance affecting the pressure change is believed to be the propylene and, on this basis, the consumption of propylene was judged to be almost the same during the two sequential reactions.

Figure 10:
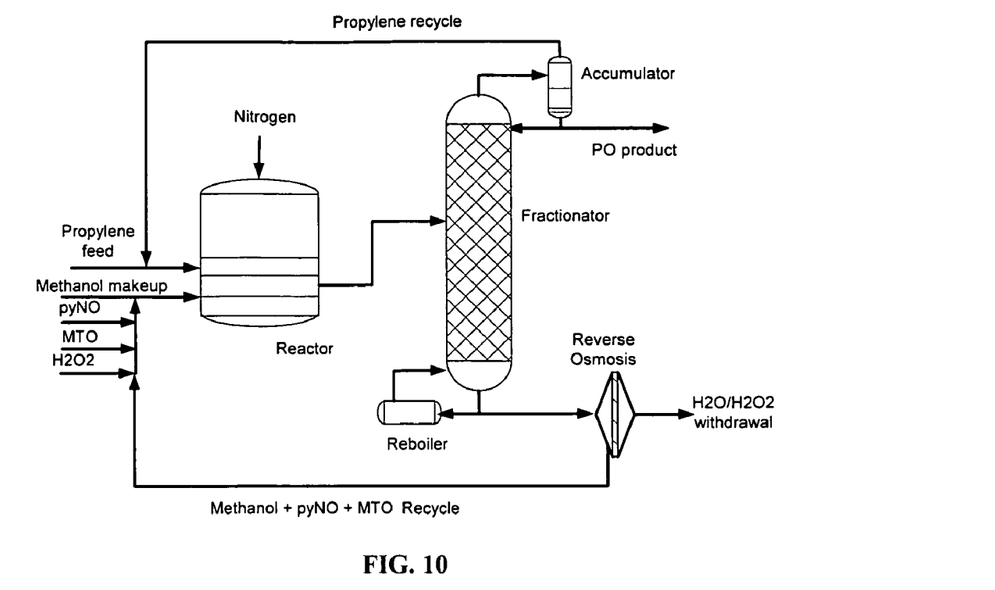
FIG. 10 is a schematic diagram of a propylene oxide process using reverse osmosis water removal system.
Figure 11:
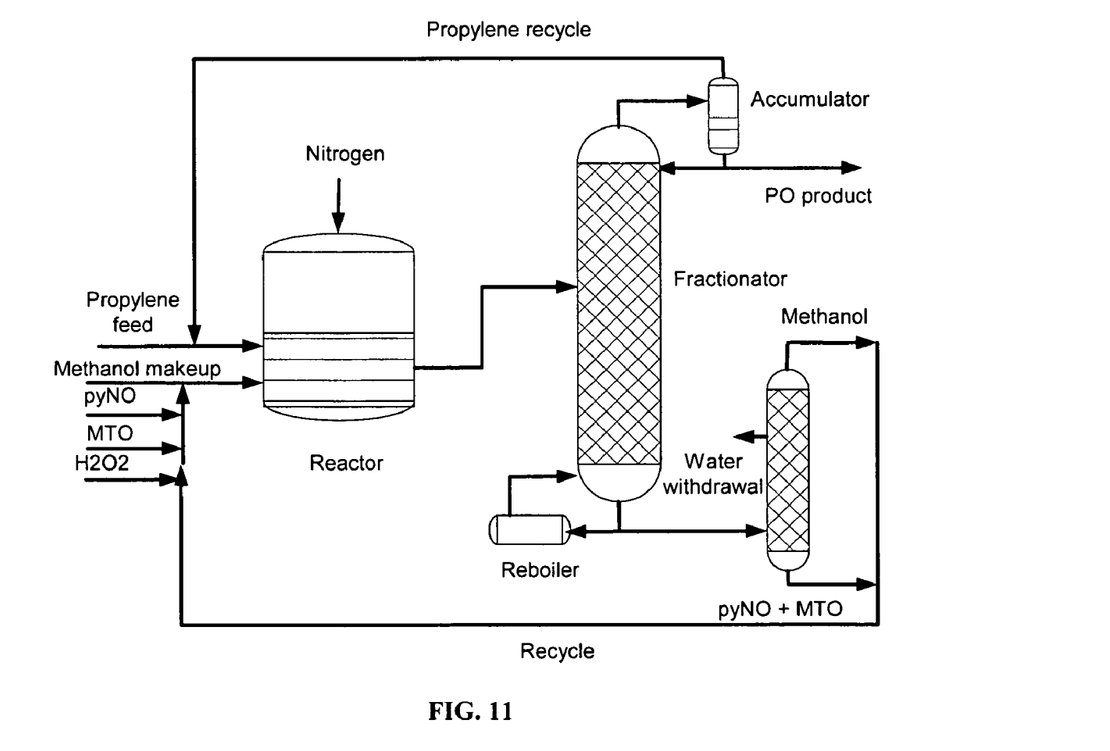
FIG. 11 is a schematic diagram of a propylene oxide production process using distillation for water separation and solvent recovery.

On the basis of the results presented herein, the most preferred reaction mixture will contain methanol, pyridine N-oxide, water, hydrogen peroxide, propylene oxide, and the MTO catalyst. Post reaction, the reactor pressure is decreased to ambient pressure causing the unreacted propylene to be released as vapor. The propylene oxide is then separated from the liquid phase by distillation around 40° C. leaving as the "bottoms product" the solvent, catalyst, and water accumulated from the water/peroxide oxidizing reagent. If methanol and catalyst are to be recycled, the main issue is separation of excess accumulated water. Reverse osmosis appears to be especially attractive to this specific system as shown in FIG. 10. Alternatively, distillation can be used for catalyst and solvent recovery as generally shown in FIG. 11.

The following are some additional considerations for these processes. First, the propylene feed position is preferentially low on the system and is directed into the liquid phase at the bottom of the tank. The feed position that returns the solvent recycle/makeup into the reactor could be higher to help absorb the propylene. However, propylene oxide would be absorbed too. Consequently, the feed position should probably be at the lower location. Second, the estimated temperature for the top/condenser would be about 30° C., the cooling water temperature to allow the condensation of PO. The bottom temperature would be in the range of 50-60° C. to promote the distillation. Lastly, the reverse osmosis ("RO") filtration is not likely to differentiate $H_2O_2$ from water. In general, small alcohol molecules are difficult to exclude from the permeate. Therefore, branched alcohols may be preferred.

From the foregoing it will be seen that this invention is one well adapted to attain all ends and objectives herein-above set forth, together with the other advantages which are obvious and which are inherent to the invention. Since many possible embodiments may be made of the invention without departing from the scope thereof, it is to be understood that all matters herein set forth or shown in the accompanying drawings are to be interpreted as illustrative, and not in a limiting sense. While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

The invention claimed is:

1. A process for epoxidizing an olefin comprising:
   contacting the olefin with an oxidant in the presence of a Lewis acid oxidation catalyst and organic base in a solvent system comprising an organic water-miscible solvent; and
   adding a pressurizing gas to increase the pressure to between 230 and 700 psi at a temperature less than 60° C., whereby said olefin is further dissolved in said organic solvent system, and whereby said olefin has an epoxidation selectivity of greater than 95%.

2. The process of claim 1 wherein said olefin is ethylene or propylene.

3. The process of claim 1 wherein said catalyst is an organorhenium oxide.

4. The process of claim 1 wherein said oxidant is hydrogen peroxide in an aqueous solution having about 20 to 80 wt % hydrogen peroxide.

5. The process of claim 1 wherein said oxidant is urea hydrogen peroxide.

6. The process of claim 1 wherein said pressurizing gas is an inert gas.

7. The process of claim 1 wherein said pressurizing gas is nitrogen having a pressure between about 230 and 700 psi.

8. The process of claim 1 wherein said organic base is a nitrogen-containing compound selected from methylamine, diethylamine, propylamine, octylamine, trimethylamine, dimethyldodecylamine, cyclohexylamine, dicyclohexylamine, aminoethanol, diethanolamine, triethanolamine, N,N-dributylethanolamine, ethylenediamine, hexamethylenediamine, morpholine, piperidine, pyridine, 2,2'-bipyridine and 2,2',2"-tripyridine and corresponding N-oxides.

9. The process of claim 1 wherein said water miscible solvent is selected from the group consisting of acetonitrile, isopropanol, tert-butanol, methanol, and other lower alcohols.

10. The process of claim 1 wherein said solvent system consists of an organic water-miscible solvent and contains no water.

11. The process of claim 1 wherein said solvent system comprises methanol and water on a weight ratio between 3:1 to 22:1 for methanol to water.

12. The process of claim 1 wherein said epoxidizing process occurs at about 20 to 30° C.

13. The process of claim 1 wherein said olefin is ethylene or propylene, said oxidant is hydrogen peroxide, said solvent system comprises methanol, said base is pyridine or pyridine N-oxide, said Lewis acid oxidation catalysis is methyltrioxorhenium, and said pressurizing gas is nitrogen having a pressure to yield a total system pressure between about 230 to 700 psi.

14. The process of claim 13 wherein said solvent system consists of an organic water-miscible solvent and contains no water.

15. The process of claim 13 wherein said solvent system consists of methanol and no water.

16. The process of claim 13 further comprising water.

17. The process of claim 1 further comprising the step of decreasing the pressure to create a vapor phase containing unreacted olefin and a liquid phase comprising the epoxidized olefin, Lewis acid oxidation catalyst, and solvent system.

18. The process of claim 17 further comprising the step of fractionating said liquid phase, thereby distilling off a first gaseous stream comprising said epoxidized olefin and forming a second liquid stream comprising said Lewis oxidation catalyst, said organic base and said solvent system comprising water and said organic water miscible solvent.

19. The process of claim 18 wherein said distilling occurs at atmospheric pressure and a temperature below about 50° C.

20. The process of claim 18 further comprising the step of separating water from said Lewis oxidation catalyst, said organic base, and said organic water miscible solvent from said second liquid stream by reverse osmosis.

21. The process of claim 20 further comprising the step of recycling said oxidation catalyst to said contacting step.

22. The process of claim 21 wherein said recycling step also comprises the step of recycling said organic base and said organic water miscible solvent to said contacting step.

23. The process of claim 18 further comprising the step of separating said oxidation catalyst, said organic base, and said organic water miscible solvent from said second stream by distillation.

24. The process of claim 23 further comprising the step of recycling said separated oxidation catalyst to said contacting step.

* * * * *

UNITED STATES PATENT AND TRADEMARK OFFICE
CERTIFICATE OF CORRECTION

PATENT NO. : 7,649,101 B2 Page 1 of 1
APPLICATION NO. : 11/586061
DATED : January 19, 2010
INVENTOR(S) : Busch et al.

It is certified that error appears in the above-identified patent and that said Letters Patent is hereby corrected as shown below:

Column 1,
Line 14, delete "Not applicable." and insert --This invention was made with U.S. Government support under Grant No. CHE-0328185, awarded by the National Science Foundation. The U.S. Government has certain rights in the invention, specifically, a paid-up license in the invention and the right in limited circumstances to require the patent owner to license others on reasonable terms as provided for by the terms of Grant No. CHE-0328185.--

Signed and Sealed this

Twentieth Day of April, 2010

David J. Kappos
*Director of the United States Patent and Trademark Office*

Disclaimer

7,649,101 B2 — Daryle H. Busch, Lawrence, KS (US); Bala Subramaniam, Lawrence, KS (US); Hyun-Jin Lee, Lawrence, KS (US); Tie-Pan Shi, Ponca City, OK (US). PROCESS FOR SELECTIVE OXIDATION OF OLEFINS TO EPOXIDES. Patent dated Jan. 19, 2010. Disclaimer filed March 1, 2011, by the assignee, University of Kansas.

The term of this patent shall not extend beyond the expiration date of Pat. No. 7,649,101.

*(Official Gazette September 6, 2011)*

UNITED STATES PATENT AND TRADEMARK OFFICE
CERTIFICATE OF CORRECTION

PATENT NO. : 7,649,101 B2
APPLICATION NO. : 11/586061
DATED : January 19, 2010
INVENTOR(S) : Daryle H. Busch et al.

It is certified that error appears in the above-identified patent and that said Letters Patent is hereby corrected as shown below:

In the Specification

Column 1,
Line 14, delete the text for "STATEMENT REGARDING FEDERALLY SPONSORED RESEARCH OR DEVELOPMENT" beginning on Line 13 and ending before the heading "BACKGROUND OF THE INVENTION" and insert the following:
--This invention was made with government support under grant numbers 0328185 AND 0310689 awarded by the National Science Foundation. The government has certain rights in the invention.--

This certificate supersedes the Certificate of Correction issued April 20, 2010.

Signed and Sealed this
Seventeenth Day of March, 2020

Andrei Iancu
*Director of the United States Patent and Trademark Office*